United States Patent [19]

Hayase et al.

[11] Patent Number: 4,648,898

[45] Date of Patent: Mar. 10, 1987

[54] TRIAZINE DERIVATIVES AND HERBICIDES

[75] Inventors: Yoshio Hayase, Mie; Koichi Morita; Kinya Ide, both of Shiga; Toshio Takahashi, Hyogo, all of Japan

[73] Assignee: Shionogi & Co., Ltd., Osaka, Japan

[21] Appl. No.: 764,252

[22] Filed: Aug. 9, 1985

[30] Foreign Application Priority Data

Aug. 15, 1984 [JP] Japan .................................. 59-170131

[51] Int. Cl.$^4$ .................... A01N 43/70; C07D 251/52; C07D 401/04; C07D 403/04
[52] U.S. Cl. .......................................... 71/93; 544/210; 544/209; 544/208; 540/598; 540/481
[58] Field of Search ...................... 544/210, 209, 208; 71/93; 540/598, 481

[56] References Cited

U.S. PATENT DOCUMENTS 3,801,537 4/1974 Westlinning et al. ............... 544/210

Primary Examiner—John M. Ford
Attorney, Agent, or Firm—Birch, Stewart, Kolasch and Birch

[57] ABSTRACT

Novel triazine derivatives (I) and herbicides are provided.

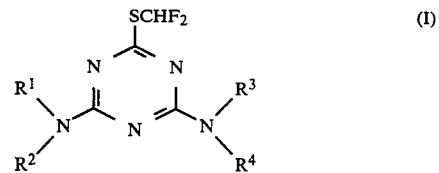

wherein $R^1$, $R^2$, $R^3$, and $R^4$ each is hydrogen, aliphatic hydrocarbon residue, lower alkoxy-(lower alkyl), cyano-(lower alkyl), or aryl-(lower alkyl); or ($R^1$ and $R^2$) or ($R^3$ and $R^4$) taken together form lower alkylene.

23 Claims, No Drawings

TRIAZINE DERIVATIVES AND HERBICIDES

BACKGROUND OF THE INVENTION

1. Field of the Invention

The present invention relates to novel triazine derivatives and herbicides containing the triazine derivatives as an effective ingredient.

2. Prior Art 2,4-diamino-1,3,5-triazine type herbicides, 2,4-bis-(isopropylamino)-6-methylthio-1,3,5-triazine (generic name: prometryn, see U.S. Pat. No. 2,909,420), 2,4-bis-(isopropylamino)-6-chloro-1,3,5-triazine (generic name: propazine, see Swiss Pat. Nos. 342,784 and 342,785), and synthetic intermediates 2,4-bis(substituted amino)-6-mercapto-1,3,5-triazine (see Swiss Pat. No. 393,344 and JPN Pat. Publn. No. 40-23025) are known. 6-difluoromethyl-1,3,5-triazine compounds, 2-amino-4-methoxy-6-difluoromethylthio-1,3,5-triazine (JPN Unexamd. Pat. Publn. No. 58-38264) are known; however, this compound is described as an intermediate to afford 2-benzenesulfonylurea, but herbicidal activities of the intermediate are not known.

BRIEF SUMMARY OF THE INVENTION

The present invention relates to the compound of the formula (I):

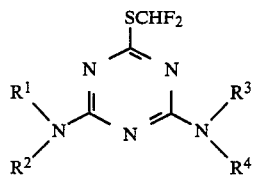

wherein $R^1$, $R^2$, $R^3$, and $R^4$ each is hydrogen, aliphatic hydrocarbon residue, lower alkoxy-(lower alkyl), cyano-(lower alkyl), or aryl-(lower alkyl); ($R^1$ and $R^2$) or ($R^3$ and $R^4$) taken together form lower alkylene or acid addition salts thereof; and it also relates to a herbical composition comprising one or more of said compounds and one or more of carriers.

The compound (I) can be prepared by reacting a mercaptotriazine with a difluoromethane derivative such as chlorodifluoromethane.

DETAILED DESCRIPTION OF THE INVENTION

The present inventors have investigated compounds having herbicidal activities and they found that novel 2,4-diamino-6-difluoromethylthio-1,3,5-triazine derivatives have potent herbicidal activities and show no or slight adverse reactions against agricultural crops or human beings. This invention is based on these findings.

The compounds of the present invention are represented by the following formula (I):

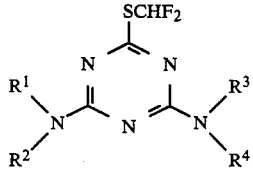

wherein $R^1$, $R^2$, $R^3$, and $R^4$ each is hydrogen, aliphatic hydrocarbon residue, lower alkoxy-(lower alkyl), cyano-(lower alkyl), or aryl-(lower alkyl); ($R^1$ and $R^2$) or ($R^3$ and $R^4$) taken together form lower alkylene.

The compounds (I) can be prepared according to the following reaction scheme:

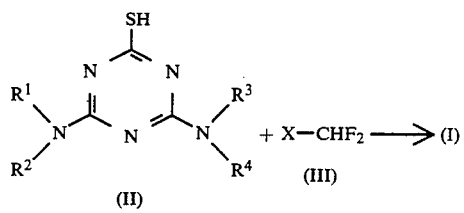

wherein $R^1$, $R^2$, $R^3$, and $R^4$ each has the same meaning as defined above; X is a leaving group.

The definitions in the above formulae are explained in more detail as follows.

The group attached by the term "lower" in the definitions means a group having not more than 7 carbon atoms, especially not more than 6 or 5 carbon atoms, unless the term is particularly defined.

"The aliphatic hydrocarbon residue" means a residue obtained by removing a hydrogen atom from saturated or unsaturated straight, branched, or cyclic aliphatic hydrocarbons.

"Saturated aliphatic hydrocarbon residue" includes straight or branched lower alkyl, in particular $C_1$–$C_{10}$ alkyl, in more particular $C_1$–$C_5$ alkyl. Examples of the alkyl are methyl, ethyl, propyl, isopropyl, butyl, isobutyl, sec-butyl, tert-butyl, pentyl, isopentyl, tert-pentyl, neo-pentyl, 1-methylbutyl, 1,2-dimethylpropyl, hexyl, heptyl, 1,3-dimethylbutyl, octyl, nonyl, decyl, and the like.

"Unsaturated aliphatic hydrocarbon residue" includes straight or branched alkenyl and alkynyl, preferably lower alkenyl and lower alkynyl, especially $C_2$–$C_6$ alkenyl and $C_2$–$C_6$ alkynyl. Representatives of the alkenyl are vinyl, allyl, isopropenyl, 2-butenyl, 1,3-butadienyl, 4-pentenyl, 5-hexenyl, and the like. The alkynyl is exemplified by ethynyl, 2-propynyl, 1-methyl-2-propynyl, 4-pentynyl, 5-hexynyl, and the like.

"Aliphatic cyclic hydrocarbon residue" means a cyclic group which is formed from a part of or all of the carbon atoms of carbon chains, i.e., cycloalkyl and cycloalkyl bound with acyclics.

"The cycloalkyl includes $C_3$–$C_7$ cycloalkyl, for example cyclopropyl, cyclobutyl, cyclopentyl, cyclohexyl, cycloheptyl, and the like.

"The lower alkoxy-(lower alkyl)" means lower alkyl which is substituted by lower alkoxy (the alkoxy is a group formed from a lower alkyl and a bivalent oxygen). The lower alkyl includes a straight or branched chain alkyl, preferably $C_1$–$C_5$ alkyl. Examples of the lower alkoxy-(lower alkyl) are methoxymethyl, ethoxyethyl, methoxypropyl, isopropoxybutyl, butoxypentyl, and the like.

"The cyano-(lower alkyl)" means lower alkyl substituted by cyano, the lower alkyl has the same meaning as defined above. Examples of the cyano-(lower alkyl) are cyanomethyl, 2-cyanoethyl, 3-cyanopropyl, 1-methyl-4-cyanobutyl, 1-cyano-1-methylethyl, etc.

"The aryl-(lower alkyl)" means lower alkyl substituted by aryl, preferably by mono-cyclic aryl, the lower alkyl has the same meaning as defined above. The aryl-(lower alkyl) is exemplified by benzyl, phenethyl, 3-tolylpropyl, 1-methyl-4-tolylbutyl, and the like.

"The lower alkylene" means straight or branched chain bivalent saturated hydrocarbon residue, preferably, $C_3$-$C_6$ alkylene, more preferably, $C_4$-$C_5$ alkylene, for example tetramethylene pentamethylene, 1-methylpentamethylene, and the like.

"The leaving group" means a group which is eliminated easily when undergoes reaction. Examples of the leaving group are acid residues such as chlorine, bromine, iodine, sulfonyloxy, p-tosyloxy, and the like.

The present invention includes acid addition salts of the compounds (I). The acid addition salt can be prepared by treating the compound (I) with an acid in a conventional manner. The acid includes inorganic acids (e.g., hydrochloric acid, sulfuric acid, phosphoric acid, nitric acid, etc.) and organic acids (e.g., acetic acid, benzoic acid, toluenesulfonic acid, picric acid, etc.).

The compound (I) can be prepared by the reaction of the compound (II) with the compound (III) as described in the above reaction scheme.

The reaction may be carried out in a solvent. As the solvent, water, high-polar organic solvents such as alkanols (e.g., methanol, ethanol, isopropanol, n-butanol, isobutanol, tert-butanol, n-pentanol, isopentanol, neopentanol, tert-pentanol, etc.) tetrahydrofuran, dioxane, N,N-dimethylformamide, dimethyl sulfoxide, etc., or a mixture thereof. Particularly, a mixture of water with a nonaqueous solvent is employed. The reaction is preferably conducted in the presence of a base (an acid-acceptor). As the base, sodium hydroxide, potassium hydroxide, sodium carbonate, potassium carbonate, and an organic amine, etc. can be employed. The reaction may be carried out at a temperature of 0°~100° C., preferably at a temperature from room temperature to the boiling point of the solvent used.

Some of the starting materials (II) are known (for instance, JPN Pat. Publn. No. 40-23025), while unknown starting materials (II) can be prepared in the same manner as the known compounds, or by the reaction of a corresponding 6-chloro compound with thiourea.

EFFECT

The compounds (I) of the present invention have excellent herbicidal activities against monocotyledonous or dicotyledonous general weeds in upland fields e.g.,

*Digitaria ciliaris* (large crabgrass),
*Setaria viridis* (green foxtail),
*Echinochloa crus-galli* (barnyard grass),
*Amaranthus viridis* (green amaranth),
*Chenopodium album* (smooth pigweed),
*Cyperus microiria* (flat-sedge),
*Mollugo stricta* (carpet-weed),
*Stellaria media* (common chickweed),
*Segina japonica* (pearlwort),
*Stellaria Alsine* (bog-stichwort),
*Capsella Bursa-pastoris* (Shepherd's purse),
*Alopecuris aequalis* (water foxtail),
*Poa annua* (annual bluegrass),
*Polygonum longisetum* (smartweed),
*Polygonum lapathifolium* (smartweed),
*Trigonotis pedunclaris* (—), and
*Gnaphalium affine* (cottonweed);
and against general weeds in paddy fields e.g.,
*Echinochloa oryzicola* (barnyard grass),
*Monchoria vaginalis* (monochoria),
*Cyperus difformis* (umbrella plant),
*Rotala indica* (tooth cup), and
*Dopatrium junceum* (—).

At the application rate of 1~40 g/are, the compounds (I) are nontoxic to common field crops such as corn, sugar cane, sorghum, rice, wheat, barley, soybean, peanut, and cotton; or a phytotoxicity in the crops, if any, is so slight that they could easily recover from the damage. Therefore, the compounds (I) can be applied as selective or non-selective herbicides to crop lands, e.g., upland fields, paddy fields, orchards, tea plantations, mulberry fields, fallow lands, and pastures; or non-corp lands, e.g., railbeds, roads, lawns, factory sites, dry riverbeds, residential quarters, park green districts, forest lands, prepared lands, and vacant lands.

Furthermore, the compounds (I) are harmless to human beings, domestic animals, and birds or poultry, and show an extremely low toxicity to fish. Consequently, the herbicides comprising the compounds (I) are safe and have no problems relating to the residual toxicity.

How to apply the compounds (I) as herbicides should be decided in consideration of the application purpose, objective plants, and application time. In general, the compounds (I) can be applied in soil or over leaves.

The application concentration should also be decided in consideration of the application purpose, objective plants, and application time, generally the concentration is about 1~5000 ppm.

The compounds (I) can be mixed with varous carriers and formulated as powder, granules, wettable powder, emulsion, and the like. The carriers may be solid or liquid carriers, or a mixture of both.

The solid carriers includes clay, talc, diatomaceous earth, bentonite, etc. The liquid carriers are exemplified by water, alkanols, acetone, benzene, toluene, xylene, solvent naphtha, cyclohexane, etc.

The formulatively acceptable emulsifiers, stabilizers, dispersants, suspending agents, spreaders, penetrants, wetting agents may be added to the herbicidal composition comprising the compounds (I).

The compounds (I) may be used in combination with other herbicides, for example diuron, MCP, CNP, IPC, asulum, alachlor, trifluralin, and the like and they can be used together with insecticides, fungicides, fertilizers, pesticides for soil treatment in order to extend the herbicidal spectrum and to get additive or potentiative herbicidal actions.

The herbicides of this invention can be applied over clay loam as well as the ordinary soil such as sandy loam soil, loam soil, and the like. They can be applied even to the soil (e.g., sandy loam soil) which tends to have an influence on the occurrence of the herbicidal activity.

EXAMPLE

The present invention will be explained in more detail by the following examples and the effect of this invention will be confirmed by the following experiments.

EXAMPLE 1

(Production of the Starting Material)

A mixture of 1.5 g of thiourea and 4 g of 2,4-bis(ethylamino)-6-chloro-1,3,5-triazine in a mixture of 20 ml of dioxane and 20 ml of water is refluxed with stirring for 2 hours in 100 ml flask. After cooling, the mixture is mixed with 1.6 g of 50% sodium hydroxide and stirred for 10 minutes. The resulting mixture is neutralized with hydrochloric acid and extracted with ethyl acetate. The extract is concentrated under reduced pressure to give 4 g of 2,4-bis(ethylamino-6-mercapto-1,3,5-triazine. The product can be used for preparation of the objective compound without isolation.

(Production of the Objective Compound)

To a mixture of 4 g of 2,4-bis(ethylamino)-6-mercapto-1,3,5-triazine, 20 ml of dioxane, and 20 ml of water is added to 4 g of 50% sodium hydroxide at a temperature of 0°~10° C. in a 200 ml three-necked flask.

The mixture is stirred for 30 minutes, heated to 55°~65° C., stirred for another 30 minutes, and chlorodifluoromethane gas is aspirated thereto for 4 hours. The resulting mixture is cooled, neutralized with hydrochloric acid, and extracted with chloroform. The extract is evaporated, and the resulting residue is purified by silica-gel chromatography to produce 1.5 g of 2,4-bis(ethylamino)-6-difluoromethylthio-1,3,5-triazine.

EXAMPLE 2

To a mixture of 2.8 g of 2,4-diamino-6-mercapto-1,3,5-triazine, 5.5 g of potassium carbonate, and 20 ml of N,N-dimethylformamide is added and chlorodifluoromethane gas is aspirated at a temperature of 55°~65° C. for 2 hours in a 100 ml three-necked flask. After cooling, the mixture is mixed with water and extracted with ethyl acetate. The extract is evaporated, and the resulting residue is purified by silica-gel chromatography to produce 0.8 g of 2,4-diamino-6-difluoromethylthio-1,3,5-triazine.

The physical properties of the compounds provided in Examples 1 and 2, and those of the compounds prepared in the same manner as described in Examples 1 and 2 are shown in the following Table 1.

TABLE 1

| Compd. No. | R¹ | R² | R³ | R⁴ | m.p. °C. | NMR spectrum data δ= ppm, (J$_{HF}$ = 56Hz, —CHF$_2$) Solvent: CDCl$_3$, (Spectra of Compds. 1 and 2 were measured in DMSO-d$_6$) |
|---|---|---|---|---|---|---|
| 1 | —H | —H | —H | —H | 213~214 | 6.30(br,s,4H,—NH$_2$X2),7.70(t,1H,—CHF$_2$) |
| 2 | —H | —CH$_3$ | —H | —H | 175~175.5 | 2.78(d,3H,—CH$_3$)6.66~7.56(m,3H,—NH—,—NH$_2$),7.87(t,1H,—CHF$_2$) |
| 3 | —H | —CH$_3$ | —H | —CH$_3$ | 137~138 | 2.96(d,6H,—CH$_3$X2),5.41(br,s,2H,—NH—X2),7.76(t,1H,—CHF$_2$) |
| 4 | —H | —CH$_3$ | —H | —C$_2$H$_5$ | 67.5~68.5 | 1.20(t,3H,—CH$_3$),2.93(d,3H,—CH$_3$),3.43(m,2H,—CH$_2$—),5.41(br,s,2H,—NH—X2),7.72(t,1H,—CHF$_2$) |
| 5 | —H | —CH$_3$ | —H | —(CH$_2$)$_2$CH$_3$ | 61~62 | 0.96(t,3H,—CH$_3$),1.61(m,2H,—CH$_2$—),2.95(d,3H,—CH$_3$),3.36(dd,2H,—CH$_2$—),5.53(br,s,2H,—NH—X2),7.77(t,1H,—CHF$_2$) |
| 6 | —H | —CH$_3$ | —H | —CH(CH$_3$)$_2$ | 58~59 | 1.20(d,6H,—CH$_3$X2),2.93(d,3H,—CH$_3$),4.13(m,1H,—CH—),5.17(br,s,1H,—NH—),5.87(br,s,1H,—NH—),7.75(t,1H,—CHF$_2$) |
| 7 | —H | —CH$_3$ | —H | —(CH$_2$)$_3$CH$_3$ | 57~58 | 0.07~1.81(m,7H,—CH$_3$,—CH$_2$—X2),2.91(d,3H,—CH$_3$),3.36(dd,2H,—CH$_2$—),5.38(br,s,2H,—NH—X2),7.70(t,1H,—CHF$_2$) |
| 8 | —H | —CH$_3$ | —H | —CH(CH$_3$)CH$_2$CH$_3$ | 78~79 | 0.92(t,3H,—CH$_3$),1.19(d,3H,—CH$_3$),1.48(m,2H,—CH$_2$—),2.94(d,3H,—CH$_3$),4.00(m,1H,—CH—),5.06(br,s,1H,—NH—),5.62(br,s,1H,—NH—),7.76(t,1H,—CHF$_2$) |
| 9 | —H | —CH$_3$ | —H | —CH$_2$CH(CH$_3$)$_2$ | 66~67 | 0.93(d,6H,—CH$_3$X2),1.80(m,1H,—CH—),2.95(d,3H,—CH$_3$),3.23(t,2H,—CH$_2$—),5.67(br,s,2H,—NH—X2),7.78(t,1H,—CHF$_2$) |
| 10 | —H | —CH$_3$ | —H | —C(CH$_3$)$_3$ | 101.5~102.5 | 1.43(s,9H),—CH$_3$X3),2.93(d,3H,—CH$_3$),5.18(br,s,1H,—NH—),5.62(br,s,1H,—NH—),7.68(t,1H,—CHF$_2$) |
| 11 | —H | —CH$_3$ | —H | —CH(CH$_3$)CH(CH$_3$)$_2$ | oil | 0.90(d,6H,—CH$_3$X2),1.12(d,3H,—CH$_3$),1.71(m,1H,—CH—),2.93(d,3H,—CH$_3$),3.93(m,1H,—CH—),5.09(br,s,1H,—NH—),5.67(br,s,1H,—NH—),7.72(t,1H,—CHF$_2$) |
| 12 | —H | —CH$_3$ | —H | —(CH$_2$)$_2$CN | 111~112 | 2.68(t,2H,—CH$_2$—),2.95(d,3H,—CH$_3$),3.67(dd,2H,—CH$_2$—),5.63(s,1H,—NH—),6.03(br,s,1H,—NH—),7.70(t,1H,—CHF$_2$) |
| 14 | —H | —CH$_3$ | —H | —CH$_2$CH=CH$_2$ | oil | 2.99(d,3H,—CH$_3$),4.06(t,2H,—CH$_2$—),5.00~6.31(m,5H,—CH$_2$—,—CH—,—NH—X2),7.80(t,1H,—CHF$_2$) |
| 15 | —H | —CH$_3$ | —H | —CH$_2$—C≡CH | 103~104 | 2.24(t,1H,≡CH),2.97(d,3H,—CH$_3$),4.20(dd,2H,—CH$_2$—),5.77(br,s,2H,—NH—X2),7.77(t,1H,—CHF$_2$) |
| 16 | —H | —CH$_3$ | —H | —(CH$_2$)$_3$OCH$_3$ | 90~91 | 1.84(m,2H,—CH$_2$),2.96(d,3H,—CH$_3$),3.24~3.78(m,7H,—CH$_3$,—CH$_2$—X2),5.82(br,s,2H,—NH—X2),7.82(t,1H,—CHF$_2$) |
| 17 | —H | —CH$_3$ | —H | ▽ | oil | 0.36~1.00(m,4H,—CH$_2$—X2),2.78(m,1H,—CH—),2.94(d,3H,—CH$_3$),5.72(br,s,1H,—NH—),5.93(br,s,1H,—NH—),7.80(t,1H,—CHF$_2$) |
| 17a | —H | —CH$_3$ | —H | —(CH$_2$)$_2$CH(CH$_3$)$_2$ | 50~51 | 0.93(d,6H,—CH$_3$X2),1.50(m,3H,—CH$_2$—,—CH—),2.95(d,3H,—CH$_3$),3.43(m,2H,—CH$_2$—),5.23~6.10(br,s,2H,—NH—X2),7.80(t,1H,—CHF$_2$) |
| 17b | —H | —CH$_3$ | —H | —(CH$_2$)$_4$CH$_3$ | oil | 0.68~1.86(m,9H,—CH$_2$—X3,—CH$_3$),2.92(d,3H,—CH$_3$),3.36(m,2H,—CH$_2$—),5.30~6.23(br,s,2H,—NH—X2),7.73(t,1H,—CHF$_2$) |
| 18 | —H | —C$_2$H$_5$ | —H | —H | 96~97 | 1.20(t,3H,—CH$_3$),3.40(m,2H,—CH$_2$—),5.53(br,s,3H,—NH—,—NH$_2$),7.71(t,1H,—CHF$_2$) |
| 19 | —H | —C$_2$H$_5$ | —H | —C$_2$H$_5$ | 91~92 | 1.20(t,6H,—CH$_3$X2),3.40(m,4H,—CH$_2$—X2),5.20(br,s,2H,—NH—X2),7.77(t,1H,—CHF$_2$) |
| 20 | —H | —C$_2$H$_5$ | —H | —(CH$_2$)$_2$CH$_3$ | 52~53 | 0.80~1.87(m,8H,—CH$_3$X2,—CH$_2$—),3.32(m,4H,—NH—X2),5.50(br,s,2H,—NH—X2) |
| 21 | —H | —C$_2$H$_5$ | —H | —CH(CH$_3$)$_2$ | 60~61 | 1.00~1.33(m,9H,—CH$_3$X3),3.40(m,2H,—CH$_2$—),4.13(m,1H,—CH—),5.20(br,s,2H,—NH—X2),7.73(t,1H,—CHF$_2$) |
| 22 | —H | —C$_2$H$_5$ | —H | —(CH$_2$)$_3$CH$_3$ | oil | 0.67~1.90(m,10H,—CH$_3$X2,—CH$_2$—X2),3.42(m,4H,—CH$_2$—X2),5.47(br,s,2H,—NH—X2) |
| 23 | —H | —C$_2$H$_5$ | —H | —CH(CH$_3$)CH$_2$CH$_3$ | oil | 0.76~1.83(m,11H,—CH$_3$X3,—CH$_2$—),3.39(m,2H,—CH$_2$—),3.95(m,1H, |

TABLE 1-continued

| Compd. No. | Substituent [Formula (I)] R¹ | R² | R³ | R⁴ | m.p. °C. | NMR spectrum data δ= ppm, ($J_{HF}$ = 56Hz, —CHF₂) Solvent: CDCl₃, (Spectra of Compds. 1 and 2 were measured in DMSO-d₆) |
|---|---|---|---|---|---|---|
| 24 | —H | —C₂H₅ | —H | —CH₂CH(CH₃)₂ | 55~56 | 0.92(d,6H,—CH₃X2),1.17(t,3H,—CH₃),1.78(m,1H,—CH—),3.30(m,4H,—CH₂—X2),5.47(br,s,2H,—NH—X2),7.72(t,1H,—CHF₂) |
| 25 | —H | —C₂H₅ | —H | —C(CH₃)₃ | 88~89 | 1.18(t,3H,—CH₃),1.42(s,9H,—CH₃X3),3.40(m,2H,—CH₂—),5.15(br,s,2H,—NH—X2),7.68(t,1H,—CHF₂) |
| 26 | —H | —C₂H₅ | —H | —(CH₂)₄CH₃ | oil | 0.69~1.76(m,12H,—CH₃X2,—CH₂—X3),3.46(m,4H,—CH₂—X2),5.41(br,s,2H,—NH—X2),7.75(t,1H,—CHF₂) |
| 27 | —H | —C₂H₅ | —H | —CH(CH₃)(CH₂)₂CH₃ | oil | 0.68~1.63(m,13H,—CH₃X3,—CH₂—X2),3.39(m,2H,—CH₂—),4.03(m,1H,—CH—),4.80~5.70(m,2H,—NH—X2),7.68(t,1H,—CHF₂) |
| 28 | —H | —C₂H₅ | —H | —(CH₂)₂CH(CH₃)₂ | 39~41 | 0.83~1.83(m,12H,—CH₃X3,—CH₂—,—CH—),3.36(m,4H,—CH₂—X2),5.36(br,s,2H,—NH—X2),7.86(t,1H,—CHF₂) |
| 29 | —H | —C₂H₅ | —H | —CH(CH₃)CH(CH₃)₂ | oil | 0.78~1.37(m,12H,—CH₃X4),1.73(m,1H,—CH—),3.39(m,2H,—CH₂—),3.92(m,1H,—CH—),5.13(br,s,2H,—NH—X2),7.71(t,1H,—CHF₂) |
| 30 | —H | —C₂H₅ | —H | —(CH₂)₂CN | 118~119 | 1.20(t,3H,—CH₃),2.68(t,2H,—CH₂—),3.50(dd,2H,—CH₂—),3.65(dd,2H,—CH₂—),5.60(br,s,1H,—NH—),6.23(br,s,1H,—NH),7.70(1H,t,—CHF₂) |
| 32 | —H | —C₂H₅ | —H | —CH₂CH=CH₂ | 62~63 | 1.17(t,3H,—CH₃),3.37(m,2H,—CH₂—),3.95(t,2H,—CH₂—),4.93~6.13(m,5H,—NH—X2,—CH—,—CH═),7.63(t,1H,—CHF₂) |
| 33 | —H | —C₂H₅ | —H | —CH₂C≡CH | 113.5~114.5 | 1.23(t,3H,—CH₃),2.28(t,1H,≡CH),3.48(m,2H,—CH₂—),4.23(dd,2H,—CH₂—),5.57(br,s,1H,—NH—),5.87(br,s,1H,—NH—),7.80(t,1H,—CHF₂) |
| 34 | —H | —C₂H₅ | —H | —(CH₂)₃OCH₃ | 77~78 | 1.17(t,3H,—CH₃),1.85(m,2H,—CH₂—),3.10~3.67(m,9H,—CH₃,—CH₂—X3),5.27(br,s,1H,—NH—),5.53(br,s,1H,—NH—),7.67(t,1H,—CHF₂) |
| 35 | —H | —C₂H₅ | —H | △ | 65~66 | 0.46~0.95(m,4H,—CH₂—X2),1.20(t,3H,—CH₃),2.72(m,1H,—CH—),3.40(m,2H,—CH₂—),5.61(br,s,2H,—NH—X2),7.72(t,1H,—CHF₂) |
| 36 | —H | —C₂H₅ | —H | ⬠ | 72~73 | 0.94~2.27(m,11H,—CH₃,—CH₂—X4),3.40(m,2H,—CH₂—),4.21(m,1H,—CH—),5.21(br,s,2H—NH—X2),7.68(t,1H,CHF₂) |
| 37 | —H | —C₂H₅ | —H | ⬡ | 69~70 | 0.79~2.22(m,13H,—CH₃,—CH₂—X5),3.43(m,2H,—CH₂—),3.81(br,s,1H,—CH—),5.20(br,s,2H—NH—X2),7.80(t,1H,CHF₂) |
| 38 | —H | —C₂H₅ | | —CH₂—(CH₂)₃CH₂— | 140~141 | 1.20(t,3H,—CH₃),1.63(br,s,6H,—CH₂—X3),3.40(m,2H,—CH₂—),3.70(br,s,4H,—CH₂—X2),5.13(br,s,1H,—NH—),7.71(t,1H,—CHF₂) |
| 40 | —H | —C₂H₅ | —C₂H₅ | —C₂H₅ | 129~130 | 1.00~1.40(m,9H,—CH₃X3),3.17~3.80(m,6H,—CH₂X3),5.27(br,s,1H,—NH—),7.77(t,1H,—CHF₂) |
| 41 | —H | —CH(CH₃)₂ | —H | —H | 77~78 | 1.20(d,6H,—CH₃X2),4.11(m,1H,—CH—),5.13~5.80(m,3H,—NH—,—NH₂),7.73(t,1H,—CHF₂) |
| 42 | —H | —CH(CH₃)₂ | —H | —(CH₂)₂CH₃ | oil | 0.92(t,3H,—CH₃),1.17(d,6H,—CH₃X2),1.53(m,2H,—CH₂—),3.25(dd,2H,—CH₂—),4.03(m,1H,—CH—),5.08(br,s,2H,—NH—X2),7.58(t,1H,—CHF₂) |
| 43 | —H | —CH(CH₃)₂ | —H | —CH(CH₃)₂ | 56~57 | 1.20(d,12H,—CH₃X4),4.10(m,2H,—CH—X2),5.00(br,s,2H,—NH—X2),7.67(t,1H,—CHF₂) |
| 44 | —H | —CH(CH₃)₂ | —H | —(CH₂)₃CH₃ | oil | 0.72~1.79(m,13H,—CH₃X3,—CH₂—X2),3.38(dd,2H,—CH₂—),4.15(m, |

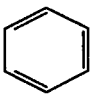

TABLE 1-continued

| Compd. No. | Substituent [Formula (I)] R¹ | R² | R³ | R⁴ | m.p. °C. | NMR spectrum data δ= ppm, ($J_{HF}$ = 56Hz, —CHF₂) Solvent: CDCl₃, (Spectra of Compds. 1 and 2 were measured in DMSO-d₆) |
|---|---|---|---|---|---|---|
| 62 | —H | —CH(CH₃)₂ | —C₂H₅ | —C₂H₅ | 58~59 | 4.11(m,1H,—CH—),4.90(br,s,1H,—NH—),7.74(t,1H,—CHF₂)1.15(m,12H,—CH₃X4),3.53(dd,4H,—CH₂—X2),4.08(m,1H,—CH—),4.97(br,s,2H,—NH—X2),7.68(t,1H,—CHF₂) |
| 63 | —H | —CH₂CH=CH₂ | —H | —CH₂CH=CH₂ | 55~56 | 4.00(t,4H,—CH₂—X2),5.00~6.26(m,8H,—CH₂—X2,—CH—X2,—NH—X2),7.72(t,1H,—CHF₂) |
| 64 | —H | —(CH₂)₃OCH₃ | —H | —(CH₂)₃OCH₃ | 81~83 | 1.80(m,4H,—CH₂—X2),3.20~3.70(m,14H,—CH₃X2,—CH₂—X4),5.70(br,s,2H,—NH—X2),7.70(t,1H,—CHF₂) |
| 65 | —H | —C₂H₅ | —CH₃ | —CH₃ | 130~131 | 1.19(t,3H,—CH₃),3.10(s,6H,—CH₃X2),3.40(m,2H,—CH₂—),5.23(br,s,1H,—NH—),7.74(t,1H,—CHF₂) |
| 66 | —H | —CH(CH₃)₂ | —CH₃ | —CH₃ | 48~49 | 1.20(d,6H,—CH₃X2),3.11(s,6H,—CH₃X2),4.16(m,1H,—CH—),5.10(m,1H,—NH—),7.74(t,1H,—CHF₂) |
| 67 | —H | —C₂H₅ | —H | —(CH₂)₅CH₃ | oil | 0.68~0.89(m,14H,—CH₂—X4,—CH₃X2),3.42(m,4H,—CH₂—X2),5.40(br,s,2H,—NH—X2),7.79(t,1H,—CHF₂) |
| 68 | —H | —CH(CH₃)₂ | —H | —(CH₂)₅CH₃ | oil | 0.65~0.83(m,17H,—CH₂—X4,—CH₃X3),3.37(m,2H,—CH₂—)4.09(m,1H—CH—,5.20(br,s,2H—NH—X2),7.75(t,1H,—CHF₂) |
| 69 | —H | —C₂H₅ | —H | —(CH₂)₆CH₃ | oil | 0.63~1.85(m,16H,—CH₂—X5,—CH₃X2),3.40(m,4H,—CH₂—X2),5.43(br,s,2H,—NH—X2),7.72(t,1H,—CHF₂) |
| 70 | —H | —C₂H₅ | —H | —(CH₂)₇CH₃ | oil | 0.57~1.73(m,18H,—CH₂—X6,—CH₃X2),3.35(m,4H,—CH₂—X2),5.49(br,s,2H,—NH—X2),7.76(t,1H,—CHF₂) |
| 71 | —H | —CH₃ | —H | —C(CH₃)₂CH₂C(CH₃)₃ | 67~68 | 0.98(s,9H,—CH₃X3),1.47(s,6H,—CH₃X2),1.86(s,2H,—CH₂—),2.93(d,3H,—CH₃—),5.18(br,s,1H,—NH—),5.94(br,s,1H,—NH—),7.71(t,1H,—CHF₂) |
| 72 | —H | —C₂H₅ | —H | —C(CH₃)₂CH₂C(CH₃)₃ | 73~74 | 0.98(s,9H,—CH₃X3),1.20(t,3H,—CH₃)1.48(s,6H,—CH₃X2),3.41(m,2H,—CH₂—),1.88(s,2H,—CH₂—)5.20(br,s,1H,—NH—),5.80(br,s,1H,—NH—),7.73(t,1H,—CHF₂) |
| 73 | —H | —CH(CH₃)₂ | —H | —C(CH₃)₂CH₂C(CH₃)₃ | 85~86 | 0.98(s,9H,—CH₃X3),1.20(d,6H,—CH₃X2),1.42(s,6H,—CH₃X2)1.79(s,2H,—CH₂—),4.40(m,1H,—CH—,(,5.06(br,s,2H,—NH—X2),7.67(t,1H,—CHF₂) |
| 74 | —H | —C₂H₅ | —H | —C(CH₃)₂CN | 122~123 | 1.23(t,3H,CH₃,J=7Hz),1.78(s,6H,CH₃X2),3.50(m,2H,CH₂),5.50(br,s,1H,NH),5.77(br,s,1H,NH),7.83(t,1H,CHF₂) |
| 75 | —H | —(CH₂)₂CH₃ | —H | —CH(CH₃)₂ | 43~44 | 0.95(t,6H,CH₃X2,J=7Hz),1.27~1.57(m,4H,CH₂X2),3.35(dd,4H,CH₂X2,J=7Hz),5.67(br,s,2H,NHX2),7.80(t,1H,CHF₂) |
| 76 | —H | —CH(CH₃)₂ | —H | —C(CH₃)₂CN | oil | 1.25(d,6H,CH₃X2,J=7Hz),1.78(s,6H,CH₃X2),4.17(m,1H,CH),5.10~5.63(m,2H,NHX2),7.77(t,1H,CHF₂) |
| 77 | —H | —(CH₂)₃CH₃ | —H | —(CH₂)₃CH₃ | oil | 0.70~1.83(m,14H,CH₃X2+CH₂X4),3.37(dd,4H,CH₂X2,J=7Hz),5.30(br,s,2H,NHX2),7.73(t,1H,CHF₂) |
| 78 | —H | —CH₂CH(CH₃)₂ | —H | —CH₂CH(CH₃)₂ | 51.5~53 | 0.93(d,12H,CH₃X4,J=7Hz),1.23~2.20(m,2H,CH₂X2,3.20(m,4H,CH₂X2,J=7Hz),5.30(br,s,2H,NHX2),7.73(t,1H,CHF₂) |
| 79 | —H | —CH(CH₃)CH₂CH₃ | —H | —CH(CH₃)CH₂CH₃ | 39.5~41 | 0.91(t,6H,CH₃X2,J=7Hz),1.16(d,6H,CH₃X2,J=7Hz),1.46(m,4H,CH₂X2),3.58~4.38(m,2H,CHX2),5.21(br,s,2H,NHX2),7.78(t,1H,CHF₂) |
| 80 | —H | —C(CH₃)₃ | —H | —C(CH₃)₃ | 125.5~126 | 1.42(s,18H,CH₃X6),5.15(br,s,2H,NHX2),7.70(t,1H,CHF₂) |

EXAMPLE 3

| | (Part by weight) |
|---|---|
| Effective ingredient (Compd. No. 3) | 5 |
| Dust clay | 95 |

The above components are mixed uniformly to give a powder.

EXAMPLE 4

| | (Part by weight) |
|---|---|
| Effective ingredient (Compd. No. 7) | 50 |
| Clay | 45 |
| Emal (Registered trademark, Kao Corp.) as a spreader | 5 |

The above components are mixed to give a wettable powder.

EXAMPLE 5

| | (Part by weight) |
|---|---|
| Effective ingredient (Compd. No. 20) | 20 |
| Xylene | 65 |
| Sorpol 3005X (Registered trademark, Toho Chemical Ind.) | 15 |

To a solution of the effective ingredient in xylene is added Sorpol to give an emulsion.

EXAMPLE 6

| | (Part by weight) |
|---|---|
| Effective ingredient (Compd. No. 25) | 3 |
| Sorpol 5060 (Registered trademark, Toho Chemical Ind.) as a spreader | 3 |
| Bentonite | 40 |
| Talc | 20 |
| Clay | 34 |

The above components are uniformly mixed, kneaded with water, and extruded by an extrusion granulator to give granules.

EXAMPLE 7

| | (Part by weight) |
|---|---|
| Effective ingredient (Compd. No. 35) | 3 |
| Emalgen 910 (Registered trademark, Kao Corp.) as a nonionic surface active agent | 1 |
| Solvent naphtha | 5 |
| Grain bentonite | 91 |

A solution of the effective ingredient and Emalgen in solvent naphtha is coated over grain bentonite to give granules.

EXPERIMENT 1

(1) Herbicidal Activity in Upland Conditions

(i) Pre-Emergence Test

Twenty seeds of test plants (*Digitaria ciliaris, Echinochloa crus-galli, Polygonum lapathifolium,* and *Amaranthus viridis*) were sowed on loam charged in a square pot (7.1×7.1 cm, 8 cm in depth) made of vinyl chloride. After being sowed, the seeds were covered with the loam 5 mm in depth and an aqueous suspension (Tween 20 is used at a concentration of 100 ppm as a spreader) of the test compound was applied over the surface of the loam with an automatic metal sprayer.

The suspension of the test compound was prepared by dilution with water at a concentration of 40 g/10 L and applied at a rate of 10 L/are.

(ii) Post-Emergence Test

Twenty seeds of test plants (*Digitaria ciliaris, Echinochloa crus-galli, Polygonum lapathifolium,* and *Amaranthus viridis*) were sowed on the loam charged in a square pot (7.1×7.1 cm, 8 cm in depth) made of vinyl chloride, then grown for 7 days at 28° C. in a chamber under lighting. The aqueous suspension of the test compound was applied over the foliage of the plants at the 2 leaf stage of *Digitaria ciliaris* and *Echinochloa crus-galli* and at the 1 leaf stage of *Polygonum lapathifolium* and *Amaranthus viridis*. The predetermined amount of the test compound was diluted with water and applied at a rate of 10 L/are. Tween 20 was used at a concentration of 100 ppm as a spreader.

(2) Herbicidal Activity in Paddy Conditions

The paddy field soil (sandy clay loam) was charged in a square pot (7.1×7.1 cm) and furnished with water 2 cm in depth. Fifteen seeds of test plants (i.e., *Echinochloa oryzicola* and *Monchoria vaginalis*) were sowed respectively. The successive treatment was carried out in the same manner as described in test (1): Herbicidal activity in upland fields.

In pre-emergence test, after being sowed the mixture of the test compound 40 g/are and water 10 L/are was immediately applied over the surface of water at a rate of 10 L/are.

In post-emergence test, on the 7th day after being sowed (at 2 leaf stage of *Echinochloa oryzicola* and *Monchoria vaginalis*) the mixture of the test compound was applied in the same manner as in pre-emergence test. In all of the tests, the pots were kept at 25° C. in a greenhouse. The herbicidal activity was evaluated 3 weeks after the application.

METHOD OF EVALUATION

The damage to the plants was observed by the following evaluation standards:
- 5: complete death
- 4: severe
- 3: moderate
- 2: mild
- 1: slight
- 0: none Results in the tests are summarized in Table 2.

TABLE 2

| | Pre-emergence | |
|---|---|---|
| | Upland | |
| | *Echinochloa* | Paddy |

TABLE 2-continued

| Compound Nos. | crus-galli | Digitaria ciliaris | Polygonum lapathifolium | Amaranthus viridis | Echinochloa oryzicola | Monochoria vaginalis |
|---|---|---|---|---|---|---|
| 43 | 5 | 5 | 5 | 5 | 5 | 5 |
| 51 a | 0 | 0 | 0 | 2 | 0 | 0 |
| 21 | 5 | 5 | 5 | 5 | 5 | 5 |
| 19 | 5 | 5 | 5 | 5 | 5 | 5 |
| 6 | 5 | 5 | 5 | 5 | 5 | 5 |
| 10 | 5 | 5 | 5 | 5 | 5 | 5 |
| 25 | 3 | 5 | 5 | 5 | 5 | 5 |
| 12 | 2 | 4 | 5 | 5 | 3 | 5 |
| 52 | 1 | 4 | 5 | 5 | 4 | 5 |
| 9 | 0 | 0 | 2 | 0 | 5 | 5 |
| 47 | 1 | 1 | 2 | 4 | 5 | 5 |
| 46 | 5 | 5 | 5 | 5 | 2 | 4 |
| 30 | 4 | 5 | 5 | 5 | 5 | 5 |
| 20 | 3 | 4 | 5 | 1 | 5 | 5 |
| 33 | 4 | 5 | 5 | 5 | 5 | 5 |
| 24 | 5 | 5 | 5 | 5 | 5 | 5 |
| 32 | 5 | 5 | 5 | 5 | 5 | 5 |
| 45 | 5 | 5 | 5 | 5 | 5 | 5 |
| 42 | 5 | 5 | 5 | 5 | 5 | 5 |
| 55 | 4 | 5 | 5 | 5 | 5 | 5 |
| 34 | 5 | 5 | 4 | 5 | 5 | 5 |
| 62 | 1 | 4 | 5 | 5 | 0 | 0 |
| 35 | 5 | 5 | 5 | 5 | 5 | 5 |
| 50 | 5 | 5 | 5 | 5 | 5 | 5 |
| 23 | 5 | 5 | 5 | 5 | 5 | 5 |
| 54 | 5 | 5 | 5 | 5 | 5 | 5 |
| 57 | 5 | 5 | 5 | 5 | 5 | 5 |
| 56 | 5 | 5 | 5 | 5 | 5 | 5 |
| 37 | 1 | 3 | 4 | 5 | 2 | 5 |
| 3 | 4 | 5 | 5 | 5 | 5 | 5 |
| 14 | 0 | 1 | 4 | 4 | 5 | 5 |
| 64 | 0 | 0 | 5 | 5 | 5 | 5 |
| 48 | 1 | 5 | 5 | 5 | 5 | 5 |
| 63 | 0 | 0 | 1 | 0 | 0 | 0 |
| 40 | 0 | 0 | 3 | 1 | 0 | 0 |
| 36 | 1 | 5 | 5 | 5 | 5 | 5 |
| 4 | 5 | 5 | 5 | 5 | 5 | 5 |
| 58 | 2 | 5 | 5 | 5 | 5 | 5 |
| 16 | 5 | 4 | 5 | 5 | 5 | 5 |
| 5 | 3 | 4 | 3 | 5 | 5 | 5 |
| 38 | 0 | 0 | 3 | 0 | 0 | 0 |
| 60 | 0 | 0 | 0 | 0 | 0 | 0 |
| 18 | 5 | 4 | 5 | 5 | 0 | 0 |
| 8 | 3 | 5 | 5 | 5 | 5 | 5 |
| 27 | 5 | 5 | 5 | 5 | 5 | 5 |
| 17 | 5 | 5 | 5 | 5 | 5 | 5 |
| 15 | 5 | 5 | 5 | 5 | 5 | 5 |
| 26 | 4 | 5 | 5 | 5 | 5 | 5 |
| 41 | 4 | 5 | 5 | 5 | 5 | 5 |
| 49 | 3 | 5 | 5 | 5 | 5 | 5 |
| 59 | 1 | 4 | 5 | 5 | 5 | 5 |
| 7 | 0 | 5 | 5 | 5 | 5 | 5 |
| 44 | 1 | 5 | 5 | 5 | 5 | 5 |
| 1 | 0 | 0 | 0 | 0 | 0 | 0 |
| 28 | 5 | 5 | 5 | 5 | 4 | 5 |
| 22 | 5 | 5 | 5 | 5 | 5 | 5 |
| 66 | 5 | 5 | 5 | 5 | 4 | 5 |
| 65 | 2 | 5 | 5 | 5 | 4 | 3 |
| 17 a | 4 | 5 | 4 | 5 | 4 | 5 |
| 2 | 2 | 3 | 4 | 5 | 4 | 3 |
| 68 | 4 | 4 | 4 | 5 | 4 | 5 |
| 67 | 5 | 5 | 5 | 5 | 4 | 5 |
| 69 | 4 | 4 | 4 | 4 | 5 | 5 |
| 71 | 0 | 0 | 3 | 4 | 4 | 5 |
| 72 | 0 | 0 | 5 | 4 | 2 | 5 |
| 29 | 5 | 5 | 5 | 5 | 5 | 5 |
| 51 | 4 | 5 | 5 | 5 | 5 | 5 |
| 11 | 5 | 5 | 5 | 5 | 5 | 5 |
| 70 | 1 | 1 | 3 | 5 | 3 | 5 |
| 17 b | 1 | 1 | 3 | 5 | 2 | 5 |
| 74 | 4 | 5 | 5 | 5 | 4 | 4 |
| 75 | 5 | 5 | 5 | 5 | 4 | 4 |
| 76 | 3 | 5 | 5 | 5 | 5 | 5 |
| 78 | 4 | 5 | 3 | 4 | 5 | 5 |
| 79 | 4 | 5 | 5 | 5 | 5 | 3 |

| | Post-emergence | | | | | |
|---|---|---|---|---|---|---|
| | Upland | | | | Paddy | |
| Compound | Echinichloa crus- | Digitaria | Polygonum | Amaranthus | Echinochloa | Monochoria |

TABLE 2-continued

| Nos. | galli | ciliaris | lapathifolium | viridis | oryzicola | vaginalis |
|---|---|---|---|---|---|---|
| 43 | 5 | 5 | 5 | 5 | 5 | 5 |
| 51 a | 4 | 4 | 5 | 5 | 0 | 4 |
| 21 | 5 | 5 | 5 | 5 | 5 | 5 |
| 19 | 5 | 5 | 5 | 5 | 5 | 5 |
| 6 | 5 | 5 | 5 | 5 | 5 | 5 |
| 10 | 5 | 5 | 5 | 5 | 5 | 5 |
| 25 | 4 | 5 | 5 | 5 | 5 | 5 |
| 12 | 4 | 4 | 5 | 5 | 5 | 5 |
| 52 | 3 | 3 | 5 | 5 | 5 | 5 |
| 9 | 2 | 4 | 5 | 5 | 5 | 5 |
| 47 | 2 | 5 | 5 | 5 | 4 | 4 |
| 46 | 5 | 5 | 5 | 5 | 3 | 4 |
| 30 | 4 | 5 | 5 | 5 | 5 | 5 |
| 20 | 4 | 5 | 5 | 5 | 5 | 5 |
| 33 | 5 | 5 | 5 | 5 | 5 | 5 |
| 24 | 5 | 5 | 5 | 5 | 5 | 5 |
| 32 | 5 | 5 | 5 | 5 | 5 | 5 |
| 45 | 5 | 5 | 5 | 5 | 5 | 5 |
| 42 | 5 | 5 | 5 | 5 | 5 | 5 |
| 55 | 5 | 5 | 5 | 5 | 5 | 5 |
| 34 | 5 | 5 | 5 | 5 | 5 | 5 |
| 62 | 2 | 5 | 5 | 5 | 4 | 3 |
| 35 | 5 | 5 | 5 | 5 | 5 | 5 |
| 50 | 5 | 5 | 5 | 5 | 5 | 5 |
| 23 | 5 | 5 | 5 | 5 | 5 | 5 |
| 54 | 5 | 5 | 5 | 5 | 5 | 5 |
| 57 | 5 | 5 | 5 | 5 | 5 | 5 |
| 56 | 5 | 5 | 5 | 5 | 5 | 5 |
| 37 | 4 | 4 | 4 | 5 | 5 | 5 |
| 3 | 4 | 5 | 5 | 5 | 5 | 5 |
| 14 | 4 | 4 | 5 | 5 | 5 | 5 |
| 64 | 3 | 2 | 5 | 5 | 5 | 5 |
| 48 | 4 | 5 | 5 | 5 | 5 | 5 |
| 63 | 3 | 3 | 5 | 5 | 5 | 4 |
| 40 | 0 | 1 | 5 | 5 | 0 | 0 |
| 36 | 4 | 5 | 5 | 5 | 5 | 5 |
| 4 | 5 | 5 | 5 | 5 | 5 | 5 |
| 58 | 4 | 5 | 5 | 5 | 5 | 5 |
| 16 | 5 | 5 | 5 | 5 | 5 | 5 |
| 5 | 5 | 5 | 5 | 5 | 5 | 5 |
| 38 | 4 | 4 | 5 | 5 | 0 | 0 |
| 60 | 0 | 0 | 0 | 5 | 0 | 0 |
| 18 | 5 | 5 | 5 | 5 | 5 | 5 |
| 8 | 4 | 5 | 5 | 5 | 5 | 5 |
| 27 | 5 | 5 | 5 | 5 | 5 | 5 |
| 17 | 5 | 5 | 5 | 5 | 5 | 5 |
| 15 | 5 | 5 | 5 | 5 | 5 | 5 |
| 26 | 4 | 5 | 5 | 5 | 5 | 5 |
| 41 | 4 | 5 | 5 | 5 | 5 | 5 |
| 49 | 4 | 5 | 5 | 5 | 5 | 5 |
| 59 | 4 | 5 | 5 | 5 | 5 | 5 |
| 7 | 4 | 5 | 5 | 5 | 5 | 5 |
| 44 | 4 | 5 | 5 | 5 | 5 | 5 |
| 1 | 4 | 1 | 4 | 4 | 4 | 4 |
| 28 | 5 | 5 | 5 | 5 | 5 | 5 |
| 22 | 5 | 5 | 5 | 5 | 5 | 5 |
| 66 | 3 | 5 | 5 | 5 | 5 | 5 |
| 65 | 3 | 5 | 5 | 5 | 5 | 0 |
| 17 a | 4 | 5 | 5 | 5 | 5 | 5 |
| 2 | 3 | 5 | 5 | 5 | 3 | 0 |
| 68 | 5 | 5 | 5 | 5 | 5 | 5 |
| 67 | 5 | 5 | 5 | 5 | 5 | 5 |
| 69 | 4 | 5 | 5 | 4 | 5 | 5 |
| 71 | 3 | 4 | 4 | 5 | 5 | 5 |
| 72 | 3 | 5 | 5 | 5 | 4 | 5 |
| 29 | 5 | 5 | 5 | 5 | 5 | 5 |
| 51 | 5 | 5 | 5 | 5 | 5 | 5 |
| 11 | 5 | 5 | 5 | 5 | 5 | 5 |
| 70 | 5 | 5 | 5 | 5 | 5 | 5 |
| 17 b | 5 | 5 | 5 | 5 | 4 | 5 |
| 74 | 5 | 5 | 5 | 5 | 5 | 5 |
| 75 | 5 | 5 | 5 | 5 | 5 | 5 |
| 76 | 5 | 5 | 5 | 5 | 5 | 5 |
| 78 | 5 | 5 | 5 | 5 | 5 | 5 |
| 79 | 5 | 5 | 5 | 5 | 5 | 5 |

Note:
Upland: Upland Field
Paddy: Paddy Field

EXPERIMENT 2

Test Method

Seeds of each test plant (20 seeds of weeds: *Digitaria ciliaris, Echinochloa crus-galli, Polygonum lapathifolium,* and *Amaranthus viridis;* 5 to 10 seeds or crops: corn, wheat, soybean, and cotton) were sowed on the loam charged in a square pot (7.1×7.1 cm, 10 cm in depth) made of vinyl chloride. After being sowed, the seeds of the weeds were covered with the loam 5 mm in height and the seeds of the crops were covered with the loam 1 cm in depth. In pre-emergence test, after being sowed the predetermined amount of the compound of the present invention ws diluted with water at a rate of 10 L/are and applied uniformly over the surface of the loam with an automatic hand sprayer. Tween 20 was used at a concentration of 100 ppm as a spreader.

In post-emergence test, the seeds were grown for 10 days in a greenhouse and the compound of the present invention was applied over the foliage of the plants in the same manner as in pre-emergence test at 2 leaf stage of *Digitaria ciliaris* (at 1 leaf stage of *Echinochloa crusgalli* and broad-leaved weeds), and at 3 leaf stage of corn (at 1 to 2 leaf stage of other crops).

In all of the tests, the pots were kept at 25° C. in a greenhouse. The herbicidal activity against each weed and the damage to the crops were evaluated 4 weeks after the application in the pre-emergence test and 3 weeks after the application in the post-emergence test.

Results are shown in Table 3.

The method of evaluation is the same as in Experiment 1.

TABLE 3

| | | Pre-emergence | | | | | | | |
|---|---|---|---|---|---|---|---|---|---|
| | rate | weeds | | | | crops | | | |
| Compd. Nos. | of compd (g/a) | Digitaria ciliaris | Echinochloa crus-galli | Polygonum lapathifolium | Amaranthus viridis | corn | wheat | soybean | cotton |
| 43 | 20 | 5 | 5 | 5 | 5 | 0 | 2 | 0 | 0 |
|    | 10 | 5 | 5 | 5 | 5 | 0 | 0 | 0 | 0 |
|    | 5  | 5 | 3 | 5 | 5 | 0 | 0 | 0 | 0 |
|    | 2.5| 5 | 2 | 5 | 5 | 0 | 0 | 0 | 0 |
| 21 | 20 | 5 | 5 | 5 | 5 | 0 | 1 | 1 | 0 |
|    | 10 | 5 | 5 | 5 | 5 | 0 | 0 | 0 | 0 |
|    | 5  | 5 | 2 | 5 | 5 | 0 | 0 | 0 | 0 |
|    | 2.5| 2 | 2 | 5 | 1 | 0 | 0 | 0 | 0 |
| 19 | 20 | 5 | 4 | 5 | 5 | 0 | 1 | 1 | 0 |
|    | 10 | 2 | 1 | 5 | 5 | 0 | 0 | 0 | 0 |
|    | 5  | 1 | 1 | 1 | 2 | 0 | 0 | 0 | 0 |
|    | 2.5| 1 | 0 | 0 | 0 | 0 | 0 | 0 | 0 |
| 35 | 20 | 5 | 5 | 5 | 5 | 1 | 4 | 3 | 0 |
|    | 10 | 5 | 5 | 5 | 5 | 0 | 2 | 2 | 0 |
|    | 5  | 5 | 3 | 5 | 5 | 0 | 0 | 0 | 0 |
|    | 2.5| 2 | 0 | 5 | 2 | 0 | 0 | 0 | 0 |
| 23 | 20 | 5 | 5 | 5 | 5 | 2 | 1 | 1 | 0 |
|    | 10 | 5 | 4 | 5 | 5 | 1 | 0 | 0 | 0 |
|    | 5  | 5 | 3 | 5 | 5 | 0 | 0 | 0 | 0 |
|    | 2.5| 3 | 3 | 5 | 5 | 0 | 0 | 0 | 0 |
| 55 | 20 | 0 | 2 | 5 | 5 | 0 | 0 | 0 | 0 |
|    | 10 | 0 | 0 | 0 | 3 | 0 | 0 | 0 | 0 |
|    | 5  | 0 | 0 | 0 | 2 | 0 | 0 | 0 | 0 |
|    | 2.5| 0 | 0 | 0 | 0 | 0 | 0 | 0 | 0 |
| 46 | 20 | 5 | 5 | 5 | 5 | 0 | 1 | 0 | 0 |
|    | 10 | 2 | 3 | 5 | 5 | 0 | 0 | 0 | 0 |
|    | 5  | 0 | 0 | 5 | 5 | 0 | 0 | 0 | 0 |
|    | 2.5| 0 | 0 | 5 | 5 | 0 | 0 | 0 | 0 |
| 3  | 20 | 5 | 5 | 5 | 5 | 0 | 2 | 1 | 0 |
|    | 10 | 4 | 5 | 5 | 5 | 0 | 2 | 0 | 0 |
|    | 5  | 2 | 2 | 5 | 4 | 0 | 0 | 0 | 0 |
|    | 2.5| 0 | 1 | 5 | 4 | 0 | 0 | 0 | 0 |
| 74 | 20 | 4 | 5 | 5 | 5 | 0 | 3 | 3 | 0 |
|    | 10 | 2 | 5 | 5 | 5 | 0 | 2 | 2 | 0 |
|    | 5  | 0 | 2 | 3 | 5 | 0 | 0 | 0 | 0 |
|    | 2.5| 0 | 0 | 0 | 5 | 0 | 0 | 0 | 0 |
| 76 | 20 | 5 | 5 | 5 | 5 | 1 | 3 | 3 | 2 |
|    | 10 | 2 | 5 | 5 | 5 | 1 | 1 | 2 | 0 |
|    | 5  | 2 | 3 | 5 | 5 | 0 | 0 | 0 | 0 |
|    | 2.5| 1 | 0 | 2 | 5 | 0 | 0 | 0 | 0 |
| 79 | 20 | 4 | 0 | 2 | 5 | 0 | 0 | 0 | 0 |
|    | 10 | 4 | 0 | 2 | 5 | 0 | 0 | 0 | 0 |
|    | 5  | 4 | 0 | 0 | 2 | 0 | 0 | 0 | 0 |
|    | 2.5| 3 | 0 | 0 | 2 | 0 | 0 | 0 | 0 |

| | | Post-emergence | | | | |
|---|---|---|---|---|---|---|
| | rate | weeds | | | | |
| Compd. Nos. | of compd (g/a) | Digitaria ciliaris | Echinochloa crus-galli | Polygonum lapathifolium | Amaranthus viridis | crop corn |
| 43 | 20 | 5 | 5 | 5 | 5 | 2 |
|    | 10 | 5 | 5 | 5 | 5 | 2 |
|    | 5  | 5 | 5 | 5 | 5 | 1 |
|    | 2.5| 5 | 3 | 5 | 5 | 1 |

TABLE 3-continued

| | | | | | | |
|---|---|---|---|---|---|---|
| 21 | 20 | 5 | 5 | 5 | 5 | 1 |
| | 10 | 5 | 5 | 5 | 5 | 1 |
| | 5 | 5 | 5 | 5 | 5 | 0 |
| | 2.5 | 5 | 4 | 5 | 5 | 0 |
| 19 | 20 | 5 | 5 | 5 | 5 | 2 |
| | 10 | 5 | 5 | 5 | 5 | 0 |
| | 5 | 5 | 5 | 5 | 5 | 0 |
| | 2.5 | 5 | 3 | 5 | 5 | 0 |
| 35 | 20 | 5 | 5 | 5 | 5 | 3 |
| | 10 | 5 | 5 | 5 | 5 | 3 |
| | 5 | 5 | 5 | 5 | 5 | 2 |
| | 2.5 | 5 | 5 | 5 | 5 | 2 |
| 23 | 20 | 5 | 5 | 5 | 5 | 2 |
| | 10 | 5 | 5 | 5 | 5 | 2 |
| | 5 | 5 | 5 | 5 | 5 | 2 |
| | 2.5 | 5 | 5 | 5 | 5 | 2 |
| 55 | 20 | 5 | 5 | 5 | 5 | 1 |
| | 10 | 5 | 5 | 5 | 5 | 0 |
| | 5 | 5 | 5 | 5 | 5 | 0 |
| | 2.5 | 5 | 5 | 5 | 5 | 0 |
| 46 | 20 | 5 | 5 | 5 | 5 | 2 |
| | 10 | 5 | 5 | 5 | 5 | 1 |
| | 5 | 5 | 5 | 5 | 5 | 0 |
| | 2.5 | 5 | 5 | 5 | 5 | 0 |
| 3 | 20 | 5 | 5 | 5 | 5 | 1 |
| | 10 | 5 | 5 | 5 | 5 | 0 |
| | 5 | 5 | 5 | 5 | 5 | 0 |
| | 2.5 | 4 | 5 | 5 | 5 | 0 |
| 74 | 20 | 4 | 5 | 5 | 5 | 2 |
| | 10 | 3 | 5 | 5 | 5 | 1 |
| | 5 | 3 | 3 | 5 | 5 | 1 |
| | 2.5 | 2 | 3 | 5 | 5 | 1 |
| 76 | 20 | 5 | 5 | 5 | 5 | 2 |
| | 10 | 4 | 4 | 5 | 5 | 1 |
| | 5 | 4 | 3 | 5 | 5 | 1 |
| | 2.5 | 3 | 3 | 4 | 5 | 1 |
| 79 | 20 | 5 | 5 | 5 | 5 | 2 |
| | 10 | 5 | 5 | 5 | 5 | 2 |
| | 5 | 5 | 4 | 5 | 5 | 0 |
| | 2.5 | 4 | 3 | 5 | 5 | 0 |

What we claim is:

1. A compound of the formula:

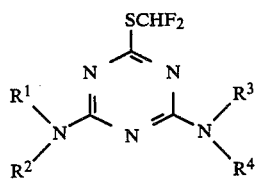

wherein $R^1$, $R^2$, $R^3$, and $R^4$ each is hydrogen, aliphatic hydrocarbon residue selected from the group consisting of $C_1$-$C_{10}$ alkyl, $C_2$-$C_6$ alkenyl, $C_2$-$C_6$ alkynyl and $C_3$-$C_7$ cycloalkyl, lower alkoxy-(lower alkyl), cyano-(lower alkyl), or $C_6$-$C_{12}$ aryl-(lower alkyl); or ($R^1$ and $R^2$) or ($R^3$ and $R^4$) taken together form lower alkylene or acid addition salts thereof.

2. The compound claimed in claim 1, wherein $R^1$, $R^2$, $R^3$, and $R^4$ each is hydrogen, $C_1$-$C_{10}$ alkyl, $C_2$-$C_6$ alkenyl, $C_2$-$C_6$ alkynyl, $C_3$-$C_7$ cycloalkyl, ($C_1$-$C_4$ alkoxy)-($C_1$-$C_5$ alkyl), cyano-($C_1$-$C_5$ alkyl), ($C_6$-$C_{12}$ aryl)-($C_1$-$C_5$ alkyl); or ($R^1$ and $R^2$) or ($R^3$ and $R^4$) taken together form $C_4$-$C_5$ alkylene.

3. The compound claimed in claim 2, wherein $R^1$ is hydrogen; $R^2$ is hydrogen, $C_1$-$C_{10}$ alkyl, $C_2$-$C_6$ alkenyl, or ($C_1$-$C_4$ alkoxy)-($C_1$-$C_5$ alkyl); $R^3$ is hydrogen or $C_1$-$C_{10}$ alkyl; $R^4$ is hydrogen, $C_1$-$C_{10}$ alkyl, $C_2$-$C_6$ alkenyl, $C_2$-$C_6$ alkynyl, $C_3$-$C_7$ cycloalkyl, ($C_1$-$C_4$ alkoxy)-($C_1$-$C_5$ alkyl), cyano-($C_1$-$C_5$ alkyl), ($C_6$-$C_{12}$ aryl)-($C_1$-$C_5$ alkyl); or $R^3$ and $R^4$ taken together form $C_4$-$C_5$ alkylene.

4. The compound claimed in claim 1, wherein $R^1$ is hydrogen; $R^2$ is hydrogen, $C_1$-$C_{10}$ alkyl, $C_2$-$C_6$ alkenyl, or ($C_1$-$C_4$ alkoxy)-($C_1$-$C_5$ alkyl); $R^3$ is hydrogen or $C_1$-$C_{10}$ alkyl; $R^4$ is hydrogen, $C_1$-$C_{10}$ alkyl, $C_2$-$C_6$ alkenyl, $C_2$-$C_6$ alkynyl, $C_3$-$C_7$ cycloalkyl, ($C_1$-$C_4$ alkoxy)-($C_1$-$C_5$ alkyl), cyano-($C_1$-$C_5$ alkyl), ($C_6$-$C_{12}$ aryl)-($C_1$-$C_5$ alkyl); or $R^3$ and $R^4$ taken together form $C_4$-$C_5$ alkylene.

5. The compound claimed in claim 1, wherein the aliphatic hydrocarbon residue is a saturated straight or branched $C_1$-$C_5$ alkyl group.

6. The compound claimed in claim 1, wherein the aliphatic hydrocarbon residue is a lower alkyl selected from the group consisting of methyl, ethyl, propyl, isopropyl, butyl, isobutyl, sec-butyl, tert-butyl, pentyl, isopentyl, tert-pentyl, neo-pentyl, 1-methylbutyl, 1,2-dimethylpropyl, hexyl, heptyl, 1,3-dimethylbutyl, octyl, nonyl and decyl.

7. The compound claimed in claim 1 wherein the aliphatic hydrocarbon residue is a residue obtained by removing a hydrogen atom from saturated or unsaturated straight, branched, or cyclic aliphatic hydrocarbons.

8. The compound claimed in claim 1 wherein the aliphatic hydrocarbon residue is an unsaturated straight or branched $C_2$-$C_6$ alkenyl or $C_2$-$C_6$ alkynyl group.

9. The compound claimed in claim 8, wherein the $C_2$-$C_6$ alkenyl is selected from the group consisting of vinyl, allyl, isopropenyl, 2-butenyl, 1,3,-butadienyl, 4-pentenyl and 5-hexenyl; and the alkynyl is selected from the group consisting of ethynyl, 2-propynyl, 1-methyl-2-propynyl, 4-pentynyl and 5-hexynyl.

10. The compound claimed in claim 1, wherein the aliphatic hydrocarbon residue includes a $C_3-C_7$ cyclic aliphatic group.

11. The compound claimed in claim 10, wherein the a $C_3-C_7$ cycloalkyl is selected from the group consisting of cyclopropyl, cyclobutyl, cyclopentyl, cyclohexyl, cycloheptyl, or a cycloalkyl bound with acyclics.

12. The compound claimed in claim 1, wherein the lower alkoxy-(lower alkyl) group is selected from the group consisting of methoxymethyl, ethoxyethyl, methoxypropyl, isopropoxybutyl and butoxypentyl.

13. The compound claimed in claim 1, wherein the cyano-(lower alkyl) is selected from the group consisting of cyanomethyl, 2-cyanoethyl, 3-cyanopropyl, 1-methyl-4-cyanobutyl and 1-cyano-1-methylethyl.

14. The compound claimed in claim 1, wherein the $C_6-C_{12}$ aryl-(lower alkyl) group includes a mono-cyclic aryl.

15. The compound claimed in claim 1, wherein the $C_6-C_{12}$ aryl-(lower alkyl) contains a substituent selected from the group consisting of benzyl, phenethyl, 3-tolypropyl and 1-methyl-4-tolylbutyl.

16. The compound claimed in claim 1, wherein the lower alkylene is selected from the group consisting of tetramethylene, pentamethylene and 1-methylpentamethylene.

17. The compound claimed in claim 2, wherein the compound is 2,4-di (iso-propylamino)-6-difluoromethyl thio-1,3,5-triazine.

18. A herbicidal composition comprising: an effective amount of at least one compound of the formula:

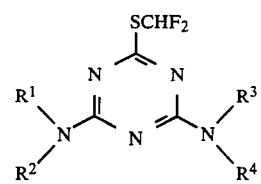

wherein $R^1$, $R^2$, $R^3$, and $R^4$ each is hydrogen, aliphatic hydrocarbon residue selected from the group consisting of $C_1-C_{10}$ alkyl, $C_2-C_6$ alkenyl, $C_2-C_6$ alkynyl and $C_3-C_7$ cycloalkyl, lower alkoxy-(lower alkyl), cyano-(lower alkyl), or $C_6-C_{12}$ aryl-(lower alkyl); or ($R^1$ and $R^2$) or ($R^3$ and $R^4$) taken together form lower alkylene or acid addition salts thereof and one or more carriers.

19. The composition claimed in claim 18, which is effective against monocotyledonous or dicotyledonous weeds in upland fields and against weeds in paddy fields.

20. The composition claimed in claim 18, wherein the carriers are solid or liquid carriers or mixture thereof or are powders, granules, wettable powders or emulsions.

21. The method for treating weeds using the compound of claim 1.

22. The method according to claim 21, wherein the application rate is 1 to 40 g/are.

23. The method according to claim 21, wherein the application concentration is about 1 to 5000 ppm.

* * * * *